United States Patent [19]
Tremblay et al.

[11] Patent Number: 6,136,308
[45] Date of Patent: Oct. 24, 2000

[54] TREATMENT OF STRESS AND PRECONDITIONING AGAINST STRESS

[75] Inventors: Johanne Tremblay; Pavel Hamet, both of Montreal, Canada

[73] Assignees: Vasogen Ireland Limited, Shannon, Ireland; Centre de Recherche du Centre Hospitalier de l'Universite de Montreal (CHUM), Montreal, Canada

[21] Appl. No.: 09/151,653

[22] Filed: Sep. 11, 1998

Related U.S. Application Data

[60] Provisional application No. 60/058,782, Sep. 12, 1997, and provisional application No. 60/059,172, Sep. 17, 1997.

[51] Int. Cl.$^7$ .................................................. C12N 5/06
[52] U.S. Cl. ........................ 424/93.7; 435/2; 435/366; 435/372
[58] Field of Search .......................... 424/93.7; 435/2, 435/366, 372

[56] References Cited

U.S. PATENT DOCUMENTS

| | | | |
|---|---|---|---|
| 4,968,483 | 11/1990 | Muller et al. | 422/45 |
| 5,591,457 | 1/1997 | Bolton | 424/613 |
| 5,891,653 | 4/1999 | Attfield | 435/7.21 |
| 5,906,636 | 5/1999 | Casscells, III et al. | 607/96 |

OTHER PUBLICATIONS

Perdrizet, G. A. et al., "Heat Shock and Recovery Protects Renal Allografts from Warm Ischemic Injury and Enhances HSP72 Production," Transplantation Proceedings vol. 25, No. 1: pp. 1670–1673, Feb. 1993.

Nishina, H. et al., "Stress–signalling kinase SEK 1 Protects Thymocytes from Apoptosis Mediated by CD 95 and CD 3," Nature, vol. 385, No. 1614, Jan. 1997.

*Primary Examiner*—Jean C. Witz
*Attorney, Agent, or Firm*—Nixon & Vanderhye

[57] ABSTRACT

Symptoms of stress such as elevated blood pressure in mammals are treated, and mammalian bodies are preconditioned to manifest reduced adverse reactions to subsequently encountered stresses, by injecting into the mammalian patient a small quantity of the patient's own blood which has been previously extracted and subjected extracorporeally to at least one stressor, such as ultraviolet radiation, an oxidative environment, ozone-oxygen and mild heating, especially infra-red radiation causing mild heating. Particularly beneficial combinations of stressors are simultaneous applications of UV radiation and an ozone-oxygen gas mixture bubbled through the blood sample to provide the oxidative environment, or simultaneous application of UV radiation, ozone-oxygen gas mixtures and mild heating. One specific use of the invention is in preconditioning against ischemic-reperfusion injury, e.g. prior to surgery.

41 Claims, 10 Drawing Sheets

TREATMENT OF STRESS AND PRECONDITIONING AGAINST STRESS

This application claims the benefit of U.S. Provisional Applications Nos. 60/058,782 filed Sep. 12, 1997, and 60/059,172 filed Sep. 17, 1997.

FIELD OF THE INVENTION

This invention relates to the field of medicine and medical treatments. In particular, it relates to stress treatment and more specifically to a method and composition for treating mammals, including humans, in order to provide them with improved reactions and resistance to stress.

BACKGROUND AND PRIOR ART

The effects of stress on a mammal normally manifest themselves in an increase in body temperature, along with a change in hemodynamic parameters, including an increase in heart rate and an increase in blood pressure. For patients already suffering from elevated blood pressure (hypertension), the effects of stress can therefore be particularly dangerous, since hypertension is a major risk factor for cardiovascular disease.

Stresses to which a mammal may be subjected, and which can result in these effects, can take a wide variety of physical forms. Psychological stresses induced by restraint, confinement, sudden exposure to danger, shock and the like translate into physical stresses affecting one or more organs of the body. Similarly, physical stress such as exposure to heat or cold, injury including surgical injury, over-exertion and the like, result in abnormal functioning of body organs. Stress is now recognized as a major detrimental factor in many diseases such as cardiovascular disease, cancer, and immunological dysfunction. Common physiological events which appear to underlie all stress responses include the induction and upregulation of synthesis, in all body cells, of a group of specialized intracellular proteins known as heat stress proteins or heat shock proteins (HSP's). These HSPs function to protect the cells from potential damage caused by whatever form of stress is being applied.

One particular species of physical stress is ischemia, which is the deprivation of oxygen resulting from reduced blood flow. Ischemia in a body organ, if severe enough, causes the eventual death of cells in the organ. Reperfusion of the ischemic organ by resumption of blood flow thereto often results in further injury to the organ due to inflammation, and does not invigorate already injured cells. Repeated application of mild ischemic Stress to an organ often leads to an increased ability to withstand stress ischemia, an effect thought to be partially related to upregulated synthesis of HSPs. Ischemia may occur as a pathological condition, e.g. as the result of spasm, thrombosis, or other blood vessel obstruction. Ischemia may be deliberately induced by clamping of blood vessels during surgery.

It is known to precondition the body of a mammalian patient by subjecting it to controlled stresses, so as better to equip the body for subsequent encounters with uncontrolled stresses of the same type. Physical exercise and training, for example, equips a body for better handling of physical exertion stresses. Heating a body or a body organ repeatedly under controlled conditions has been shown to provide the body or body organ with preconditioning for the better handling of subsequent heat stresses. Even in respect of ischemia, a body organ such as the heart which has previously suffered mild ischemia is better able to resist the effects of later ischemia, of the type causing myocardial infarction. As stated by Gersh et al., "Preconditioning is an important phenomenon, probably with clinical implications, because repetitive anginal episodes in patients may develop into full fledged infarction. Patients with pre-infarction angina may suffer from a less severe infarct than those thought to undergo sudden coronary occlusion without the opportunity for preconditioning. In contrast, patients with multiple short-lived attacks of ischemia might become tolerant through the development of protective preconditioning, according to animal data."[1] Preconditioning by subjection to heat or ischemia is however clearly impractical in respect of most mammalian bodies and body organs.

U.S. Pat. No. 4,968,483 Mueller et al., describes an apparatus for oxygenating blood, by treating an aliquot of a patient's blood, extracorporeally, with an oxygen/ozone mixture and ultraviolet light, at a controlled temperature. The apparatus is proposed for use in hematological oxidation therapy.

U.S. Pat. No. 5,591,457 Bolton, discloses a method of inhibiting the aggregation of blood platelets in a human, a method of stimulating the immune system and a method of treating peripheral vascular diseases such as Raynaud's disease, by extracting an aliquot of blood from a patient, subjecting it to ozone/oxygen gas mixture and ultraviolet radiation at a temperature in the range of about 37–43° C., and then reinjecting the treated blood into the human patient.

International Patent Application PCT/GB93/00259 Bolton, describes a similar process for increasing the content of nitric oxide in the blood of a mammalian patient, potentially useful in treating conditions such as high blood pressure in mammalian patients.

SUMMARY OF THE INVENTION

It is an object of the present invention to provide a novel method of treating stress in a mammalian patient.

It is a further object to provide a process of preconditioning a mammalian patient to improve the patient's resistance and reaction to subsequently encountered stress.

It is a further and important object of the invention to provide a means of protecting target organs against ischemia/reperfusion injury.

The present invention is based upon the discovery that an aliquot of a patient's blood, subjected extracorporeally to one or more stressors and then re-injected into the patient, has beneficial effects on the patient's subsequent abilities to withstand the adverse effects of subsequently encountered stresses, as well as beneficial effects on the symptoms of stress. According to the present information, application of selected stressors to the blood aliquot extracorporeally appears to cause changes in certain of the blood cells of the aliquot. It exerts beneficial effects [to] on the patient's blood including the increased resistance to subsequently encountered stresses as reported in more detail hereinafter.

Accordingly, from one aspect, the present invention provides a process of treating a mammalian patient to counteract the adverse effects of stress and/or to precondition the patient for improved resistance and reaction to subsequently encounter stress, which comprises extracting from the patient an aliquot of blood, subjecting the aliquot to extracorporeal application of one or more stressors thereto, and reinjecting the treated blood aliquot into the patient.

Stressors which can accordingly be used in the present invention, include oxidative stressors, heat stressors and ultraviolet radiation, alone or in combinations of two or three of such stressors, and applied simultaneously or sequentially to the blood aliquot. Thus according to a more specific aspect of the present invention, there is provided a process of treating a mammalian patient to counteract the adverse effects of stress and/or to precondition the patient for improved resistance and reaction to subsequently encountered stress, which comprises extracting from the patient an aliquot of blood, subjecting the extracted blood aliquot extracorporeally to at least one stressor selected from an oxidative environment, UV radiation and elevated temperature, and reinjecting at least a portion of the treated blood aliquot into the patient.

THE PREFERRED EMBODIMENTS

The method of the invention involves the extraction of an aliquot of blood from the patient, the subjection of the blood aliquot extracorporeally to one or more stressors and the reinjection of the treated blood aliquot into the patient. The treatment counteracts the effects of stress from which the patient is suffering at the time and shortly after the patient receives the treatment. More significantly and importantly, as a result of the treatment, preferably a series of treatments, the patient is better equipped to withstand the adverse effects of subsequently encountered stress. The treatment process according to the present invention causes the mammalian patients, when subsequently stressed, to exhibit decreased stress responses as detected by smaller rises in body temperature, smaller increases in heart rate and/or smaller increases in diastolic blood pressure.

Thus, from another aspect, the present invention provides the use, for preparing a medicament for treating stress in a patient and for preconditioning a patient to better withstand the adverse effects of subsequently encountered stress, of an aliquot of blood which has been subjected extracorporeally to at least one stressor selected from an oxidative environment, UV radiation and elevated temperature.

The size of the blood aliquot to be treated is, in the case of human patients, generally from about 0.1 ml to about 400 ml, preferably from about 0.1–100 ml and most preferably 5–15 ml, with suitable prorating according to relative body weight for non-human patients. Care must be taken not to utilize an excessive level of the stressors, to the extent that the cell membranes of the white cells of the blood are caused to be disrupted, or other irreversible damage is caused to an excessive number of the cells in the blood.

In the preferred process of the present invention, the blood aliquot can be extracorporeally subjected to the heat stressor alone, to the UV stressor alone, or to the oxidative stressor alone. It can also be extracorporeally subjected to both the heat stressor and the UV stressor, to both the heat stressor and the oxidative stressor, and to both the UV stressor and the oxidative stressor. It can also be extracorporeally subjected to all three of the heat stressor, the oxidative stressor and the UV stressor. When combinations of two or more stressors are used, they can be applied sequential in any order, or simultaneously. Particularly beneficial results are obtained by simultaneous use of two of the three stressors, especially the oxidative stressor and the UV stressor, or the simultaneous use of all three of the stressors, as demonstrated in the specific examples which follow.

The temperature stressor must keep the aliquot in the liquid phase and should not heat it above about 45° C.

The term "elevated temperature" as used herein means a temperature higher than that which the blood attains at the start of the subjection of the blood to the stressors in the process of the invention. Depending upon the precise method of handling the blood aliquot, its temperature at the start of the process could be as low as 15° C. Whilst the blood aliquot is at body temperature (c. 37° C.) when first extracted from the patient, the act of extraction, the addition of anticoagulant, the introduction into the treatment apparatus and the storage of the blood aliquot may all exercise a cooling effect on the blood, to bring its temperature down to as low as 15° C. when the process starts. Accordingly the "elevated temperature stressor" applied in the process of the invention is a heating above this introductory temperature. Any suitable source of heat known in the art may be employed to heat the blood, preferably one or more infrared lamps. Thus, in a preferred process of the present invention, the blood aliquot is subjected to infra-red radiation as a stressor, alone or in combination with the other stressors namely UV radiation and an oxidative environment, the infrared radiation normally but not necessarily causing heating of the blood aliquot.

The temperature stressor preferably warms the aliquot being treated to a temperature above normal body temperature, i.e. to about 38–44° C., and most preferably from about 38–43° C., e.g. about 42.5° C., for a period of time from about ½ to about 10 minutes, and preferably about 1–5 minutes, moat preferably about 3 minutes.

The application of the oxidative stressor preferably involves exposing the aliquot to a mixture of medical grade oxygen and ozone gas, most preferably by bubbling through the aliquot, at the aforementioned temperature range, a stream of medical grade oxygen gas having ozone as a minor component therein. The ozone gas may be provided by any conventional source known in the art. Suitably the gas stream has an ozone content of from about 1.0–100 μg/ml, preferably 3–70 μg/ml and most preferably from about 5–50 μg/ml. The gas stream is supplied to the aliquot at a rate of from about 0.01–2 liters per minute, preferably 0.05–1.0 liters per minute, and most preferably at about 0.06–0.30 liters per minute (STP). Alternative application of oxidative stressors include addition of peroxides such as hydrogen peroxide to the blood, and addition of biochemically acceptable chemical oxidizing agents such as permanganates and periodates to the blood aliquot.

The ultraviolet radiation stressor is suitably applied by irradiating the aliquot under treatment from an appropriate source of UV radiation. The ultraviolet radiation may be provided by any conventional source known in the art, for example by a plurality of low-pressure ultraviolet lamps. The method of the invention preferably utilizes a standard UV-C source of ultraviolet radiation, namely UV lamps emitting primarily in the C-band wavelengths, i.e. at wavelengths shorter than about 280 nm. Ultraviolet radiation corresponding to standard UV-A and UV-B sources can also be used. Preferably employed are low-pressure ultraviolet lamps that generate a line spectrum wherein at least 90% of the radiation has a wavelength of about 253.7 nm. An appropriate dosage of such UV radiation, applied simultaneously with the aforementioned temperature and oxidative environment stressors, is obtained from lamps with a power output of from about 5 to about 25 watts, preferably about 5 to about 10 watts, at the chosen UV wavelength, arranged to surround the sample container holding the aliquot. Each such lamp provides an intensity, at a distance of 1 meter, of from about 40–80 micro watts per square centimeter. Several such lamps surrounding the sample container, with a combined output at 253.7 nm of 15–40 watts, preferably 20–40 watts, operated at maximum intensity, may advantageously be used. At the incident surface of the blood, the UV energy supplied may be from about 0.25–4.5 $J/cm^2$ during a 3-minute exposure, preferably 0.9–1.8 $J/cm^2$. Such a treatment provides a blood aliquot which is appropriately modified according to the invention ready for re-injection into the patient.

The time for which the aliquot is subjected to the stressor(s) can be from a few seconds to about 60 minutes. It is normally within the time range of from about 0.5–60 minutes. This depends to some extent upon the chosen intensity of the UV irradiation, the temperature and the concentration of and rate at which the oxidizing agent is supplied to the aliquot. Some experimentation to establish optimum times and dosages may be necessary on the part of the operator, once the other stressor levels have been set. Under most stressor conditions, preferred times will be in the approximate range of about 0.5–10 minutes, most preferably 2–5 minutes, and normally around 3 minutes. The starting blood temperature, and the rate at which it can be warmed or cooled to a predetermined temperature, tends to vary from patient to patient.

In the practice of the preferred process of the present invention, the blood aliquot (or the separated cellular fractions of the blood, or mixtures of the separated cells, including platelets, these various leucocyte-containing combinations, along with whole blood, being referred to collectively throughout as the "aliquot") may be treated with the stressors using an apparatus of the type described in U.S. Pat. No. 4,968,483 Mueller. The aliquot is placed in a suitable, sterile, UV-radiation-transmissive container, which is then fitted into the machine. The temperature of the aliquot is adjusted to the predetermined value, e.g. 42.5±1° C., by the use of a suitable heat source such as an IR lamp, and the UV lamps are switched on for a fixed period before the gas flow is applied to the aliquot providing the oxidative stress, to allow the output of the UV lamps to stabilize. Then the oxygen/ozone gas mixture, of known composition and controlled flow rate, is applied to the aliquot, for the predetermined duration of 0.5–60 minutes, preferably 2–5 minutes and most preferably about 3 minutes as discussed above, so that the aliquot experiences all three stressors simultaneously. In this way, the blood aliquot is appropriately modified according to the present invention sufficient to achieve the desired effects.

Re-injection of the treated blood aliquot into the patient can be accomplished intravenously, intramuscularly, subcutaneously or by other common injection administration methods. Intramuscular reinjection is preferred.

The process of the present invention shows utility both in treating a patient's stress symptoms evident at the time the treatment is administered, and in preconditioning a mammalian patient against the adverse effects of subsequently encountered stress, of any of the aforementioned types. It is not specific to providing tolerance to a specific stress or type of stress, but appears to be of general application. A patient who has undergone a treatment or a series of treatments according to the process of the present invention will exhibit notably reduced adverse reactions to subsequently encountered stress, such as a notably reduced rise in body temperature and/or a reduced increase in heart rate and/or a reduced increase in diastolic blood pressure, in response to stress, as compared with a similar but untreated patient, The process is thus particularly useful for patients who are scheduled to undergo stress such as surgery at a predetermined future date. They can precondition their bodies to be ready for surgery by undergoing a treatment or a series of treatments according to the invention prior to surgery, with the result that they will withstand the surgery better and will recover from it more quickly, thus reducing the time of hospitalization.

Another preferred use of the present invention is in protecting tissues and organs from stress-induced damage, in a manner similar to ischemic preconditioning. As noted previously, repetitive mild ischemic (anginal) episodes can render tissues and organs less susceptible to stress-induced damage, by ischemic preconditioning, although application of ischemic preconditioning by current methods is largely impractical. The process of the present invention can take the place of ischemic preconditioning, ischemia being a species of physical stress. Accordingly, the process of the present invention offers potential for treatment of unstable angina and decrease of infarct size, a treatment not effectively addressed by available therapies.

Similarly, the process of the present invention is applicable in the protection of body organs destined for transplantation. Treatment of the donor body by the process of the present invention serves to protect body organs against damage resulting from the inevitable ischemia which the organ will suffer on removal from the donor body, transportation and subsequent surgical introduction into the recipient body. The treatment according to the invention extends the useful life of the transplant organ between its removal from the donor body and its surgical introduction into the recipient body, thereby reducing losses of viable transplant organs due to transportation delays.

A further, specific clinical application of the process of the invention is in treatment of patients suffering from transient ischemic attacks (TIA's, pre-strokes), which are due to temporary obstruction of blood flow to certain areas of the brain. They commonly indicate the likelihood of suffering a major stroke in the near future. Subjection of such patients to treatment according to the process of the invention, at the onset of TIA's, will precondition the brain to avoid or at least to lessen the severity of the effects of the forthcoming major stroke.

Stressors used to treat the blood aliquot in the process of the present invention and described in the experiments detailed below are among those known to have the effect of activating the SAP kinase pathway in blood cells. It is suspected that other stressors known to activate the SAP kinase pathway when applied to blood will have similar effects on the blood aliquot in the process of the invention, namely putting the blood aliquot into a condition in which, after re-injection into the patient, it will have beneficial effects on body organs in protecting them against stress as described herein. Such other stressors include gamma radiation and other forms of ionizing radiation, hyperosmolarity, chemotherapeutic agents (cisplatinum and mytomycin C, for example), inflammatory cytokines such as TNFα and IL-1, tunicamycin, anisomycin and sodium arsenite. Stress-activated protein kinases (SAPKs), also known as cJun amino-terminal kinases (JNKs), are a family of protein kinases similar to Erk-1 and Erk-2 MAPKs (mitogen-activated protein kinases). They can be activated through their signal transduction pathways (the SAP kinase pathways or SAP/JN kinase pathway) to effect their phosphorylation function. Members of the SAP kinase family include p38 HOG, JNK (Jun N-terminal kinase) and BMK-1. These same stressors are also known to activate the heat shock protein pathway.

Determination of the state of activation of the SAP kinase pathway may be a useful indicator of whether or not an aliquot of blood has been treated according to the process of the invention, rendering it ready for re-injection into the patient for stress-conditioning purposes. There are known, standard methods available and published in the literature for determining activation of the SAP kinase pathway. These include immunoprecipitation with antibodies specific for the individual SAP kinases (JNK, p38 and SAP-K3, for example), followed by phosphotyrosine blotting, which, if positive, indicates SAP kinase pathway activation.

The beneficial effects of the present invention have been demonstrated in vivo by clinical experiments on juvenile and adult rats, specifically rats of an inbred strain of genetically hypertensive rats (SHR's). Genetically hypertensive rats (SHR's) are the most widely used animal model for hypertension research, and are well known and readily available to researchers in this field. SHR's have several genetic defects, one of the most important being failure to produce appropriate amounts of HSPs when subjected to stress. SHR's develop hypertension rapidly and exhibit exaggerated increase in heart rate, blood pressure and body temperature in response to stress. They represent a model of hypersensitivity to stress. The results obtained using them provide reliable indications of potential results obtainable with human patients. The effects have also been shown by in vivo clinical experiments on dogs, detailed below in Example 8.

EXAMPLE 1

Blood from sacrificed SHR's of the same strain as the test animals was collected, treated with sodium citrate anticoagulant and pooled. A portion of the blood was then placed in a sterile container, and subjected simultaneously to the UV radiation, ozone/oxygen gas oxidative environment and elevated temperature stressors, in an apparatus as generally described in the aforementioned Mueller U.S. Pat. No. 4,968,483. More specifically, the blood sample in the sterile, UV-transparent container was heated using infrared lamps to 42.5° C., and whilst being maintained at that temperature, it was subjected to UV radiation of wavelength 253.7 nm under the preferred conditions previously described. Simultaneously, a gaseous mixture of medical grade oxygen and ozone, of ozone content 13.5–15.5 μg/ml, was bubbled through the blood sample at a rate of flow over a range from 60–240 mls/min. The time of simultaneous UV exposure and gas mixture feed was 3 minutes.

A further portion of the pooled blood, to act as a control, was similarly placed in a sterile container and placed in the aforementioned apparatus, but was not heated, nor subjected to UV radiation nor subjected to application of any ozone/oxygen gas mixture. In addition, to provide a further control, a sterile aqueous physiological saline solution was prepared.

A total of 44 seven week old SHR's were selected and divided into three groups, group A containing 15 animals, group B containing 15 animals, and group C containing 14 animals. For a period of 10 days (at 7–9 weeks of age), each animal of group A received a daily intragluteal injection of 150 μl of the UV, heat and ozone treated blood. Each animal of group B received at the same time a similar daily injection of the untreated blood. Each animal of group C received at the same time a similar injection of physiological saline.

At the age of 9 weeks, 4 days after completion of the injections the animals were anaesthetized and, a telemetry probe was inserted surgically into the femoral artery of each animal. The telemetry probe (trade-mark DATAQUEST LABPRO, available from Data Sciences International) is a commercially available probe equipped with a radio transmitter, to permit heartbeat, systolic blood pressure, diastolic blood pressure and other signals to be received and recorded without further handling of the animals, which might induce further, uncontrolled stress reactions. An additional probe was surgically inserted into the peritoneal cavity of each animal, to measure body temperature.

Continuous daily recordings of body temperature, blood pressure and heart rate were made from each animal, during the 10 day period following the surgery, readings being taken during the inactive, at-rest portion of the animals' daily cycle, i.e. the daylight ("light-on") portion, and during the activity time (night). Group A animals which received injections of blood treated according to the process of the invention demonstrated a significantly more rapid recovery of normal body temperature following surgery (6 days vs. 10 days), as compared with group B animals which received untreated blood and group C animals which received saline injections, as shown especially by the readings taken during the resting periods. The differences are less evident from night-time, activity phase readings, suggesting that the higher cortisol levels present during activity may have an influence on the results. This demonstrates a significant effect of the treatment of the present invention on lessening the mammalian body's response to the stress of surgery.

Figure 1:
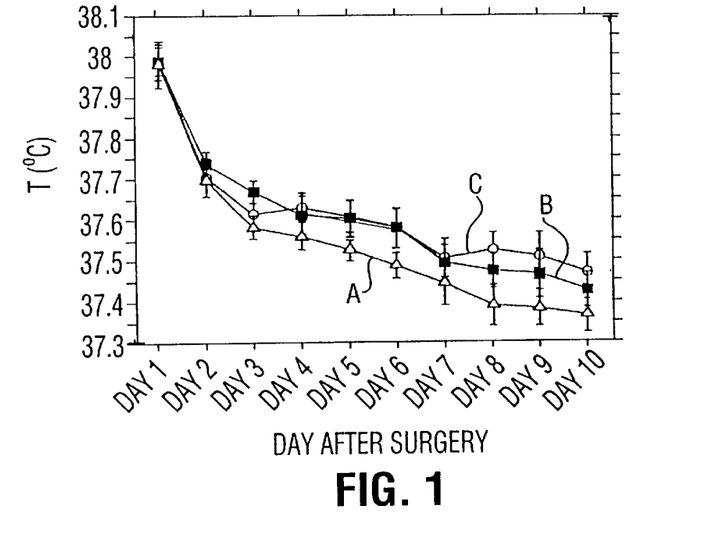
FIG. 1 is a graphical representation of the results obtained according to specific Example 1 described below.

The results of these experiments are presented graphically on FIG. 1, a plot of measured body temperatures against days after surgery, each plotted value being the mean of values obtained from the whole group during the at-rest periods. Curve A is derived from group A animals, curve B from group B animals and curve C from group C animals. The results of the saline-injected group and the untreated blood group (B v C) are not significantly different (P-value 0.6764). The results from the treated blood group are, however, significantly different (A v B, p=0.008; A v C, p=0.0002).

EXAMPLE 2

The 44 animals treated as described in Example 1, namely the Group A of 15 animals which had received injections of blood treated according to the process of the invention, Group B of 15 animals which had received injection of untreated blood, and Group C which had received injection of saline, 10 days after the probe implantation surgery described in Example 1, were subjected to psychological stress through standard immobilization stress test, by placing them in small restraint cages for a period of 30 minutes (age of animals—11 weeks). During this immobilization period, readings of body temperature, blood pressure and heart rate, at one minute intervals, were recorded.

Figure 2:
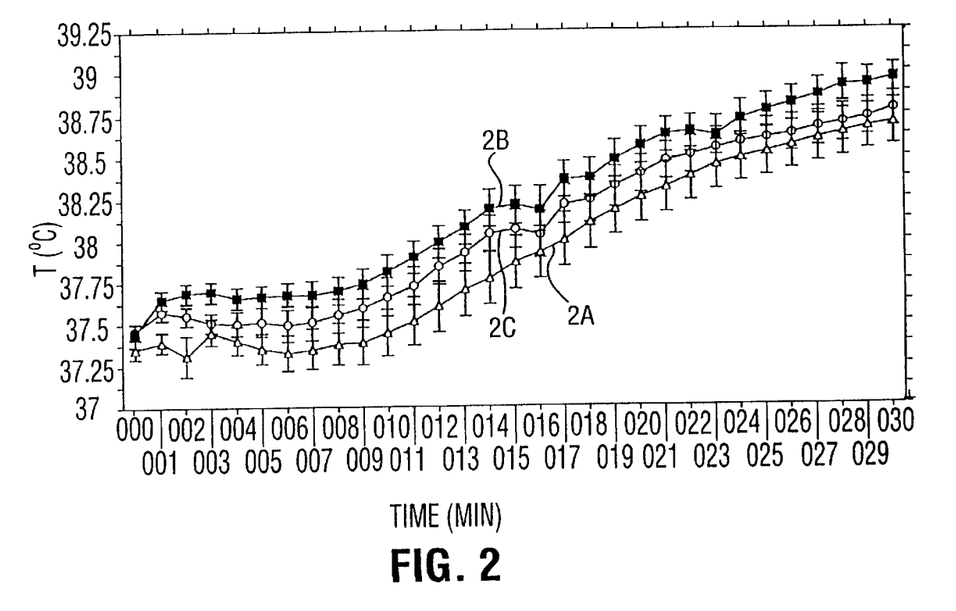
FIG. 2 is a graphical presentation of the body temperature results obtained according to Example 2 described below.

Accompanying FIG. 2 of the drawings is a graphical presentation of the results of the body temperature measurements of the three groups, namely a plot of time as ordinate against body temperature as abscissa over the 30 minute duration of the immobilization stress test. As FIG. 2 shows, curve 2A derived from experimental Group A is consistently and significantly below curve 2B obtained from control Group B and curve 2C obtained from control Group C. Statistical analysis of all the data obtained confirms the high significance of the differences in the figures obtained from experimental Group A.

Figure 3:
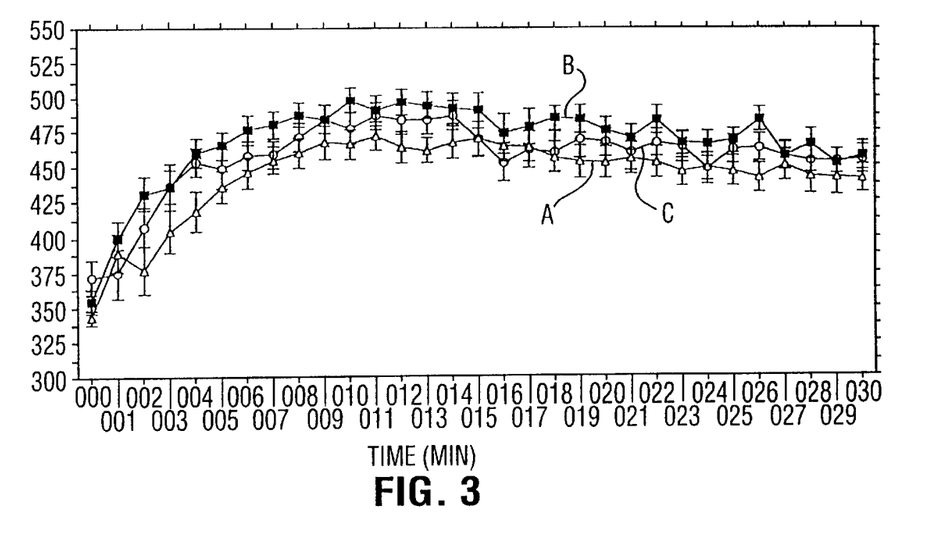
FIG. 3 is a graphical presentation of the heart rate results obtained according to Example 2 described below.

FIG. 3 of the accompanying drawings presents graphically the results of heart rate measurements on the three groups, with heart rate (beats per minute, bpm) plotted as ordinate against time of the stress test. Again, the results (averaged over the animals in each group) show that the group which received the injections of blood treated according to the invention, Group A, had a lower increase in heart rate, as compared with the other two groups, over substantially the entire duration of the test. The differences between the respective groups are statistically significant—p=0.0001 in each case.

Figure 4:
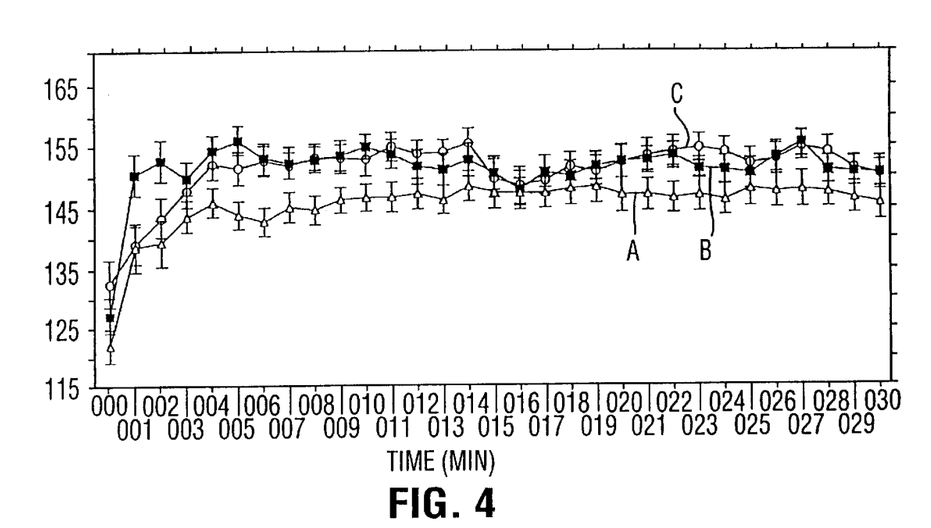
FIG. 4 is & graphical presentation of the diastolic blood pressure results obtained according to Example 2 described below.

FIG. 4 of the accompanying drawings presents graphically the results of the measurements of diastolic blood pressure of each of the three test groups, with diastolic blood pressure (mmHg) plotted as ordinate against time of the stress test. Again, the values from Group A (averaged), the group which had received injections of blood treated according to the invention, are consistently and significantly (p=0.0001 in each case) lower than those from the other two groups.

EXAMPLE 3

The Group C animals from Example 2, i.e. the control group which had, at age 7–9 weeks, received injections of physiological saline, were divided into three sub-groups Ca, Cb, and Cc. Each group was given a course of 10 daily injections of, respectively, 150 µl of the treated blood, 150 µl of the untreated blood, and 150 µl of physiological saline. The course of injection started when the animals were 12 weeks old, i.e. fully matured adults. The telemetry probes remained in place. The same 30 minute immobilization stress test was performed on each animal, at age 16 weeks, and measurement of heart rate, blood pressure and body temperature were taken.

Figure 5:
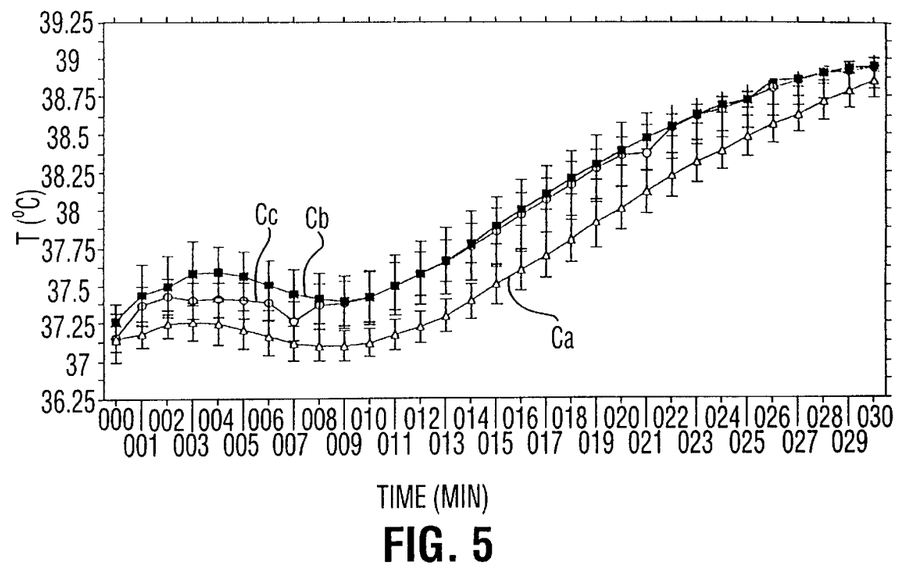
FIG. 5 is a graphical presentation of the body temperature results obtained according to Example 3 described below.

In body temperature response, the group Ca injected with blood treated according to the process of the invention showed a significantly more blunted increase during the stress period. This is illustrated in FIG. 5, a graphical presentation of the results similar to FIG. 2. It can be seen that curves Ca, derived from the Group Ca animals, is consistently lower than curve Cb derived from Group Cb animals and consistently lower than curve Cc derived from Group Cc animals. The treated blood v untreated blood results, and the treated blood v saline results are statistically significant—p=0.0001 in each case.

EXAMPLE 4

The Group A experimentally treated animals from Example 2 which had received injections of blood treated according to the invention at age 7–9 weeks were divided into three sub-groups, labelled Aa, Ab and Ac, five animals in each group. They were then subjected to a second series of 10 daily injections of 150 µl of, respectively, the treated blood, the untreated blood and the physiological saline. The course of injections started when the animals were 12 weeks old. The telemetry probes were left in place from Example 1, so that the surgery did not need to be repeated. The animals were then subjected again, at 16 weeks of age, to the same immobilization stress test as described in Example 2 for 30 minutes, and measurements taken at 1 minute intervals of heart rate, blood pressure and body temperature.

Figure 6:
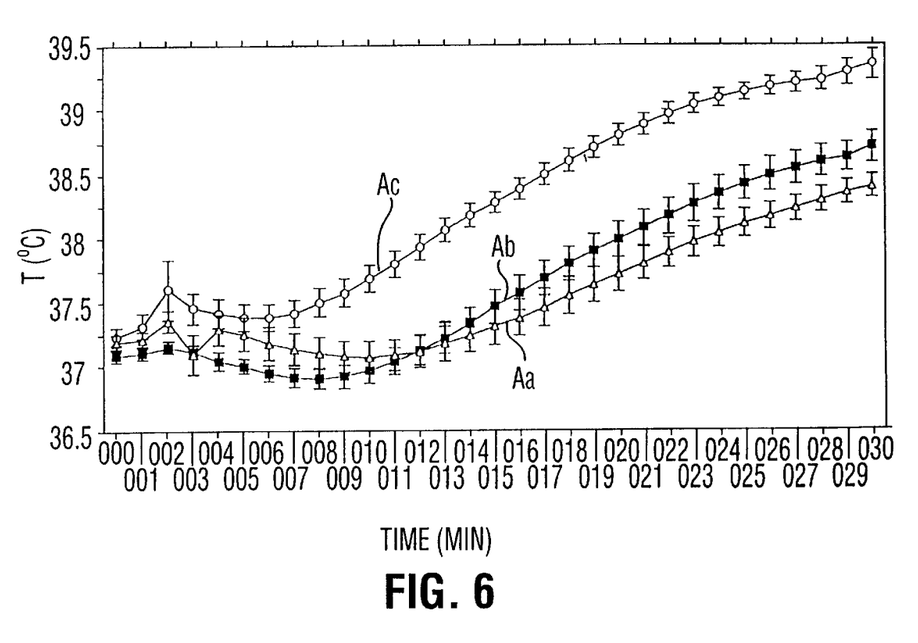
FIG. 6 is a graphical presentation of the body temperature results obtained according to Example 4 described below.

The differences between the groups with regard to body temperature rise were very significant. They are illustrated on FIG. 6, a plot of body temperature against time, based on averages, similar to FIG. 2. After about the 12th minute of the test, group Aa which had received 2 courses of injection with the blood treated according to the invention exhibited consistently and significantly (p=0.0019 or less in each case) the lowest rise in body temperature. Curve Aa derived from Group Aa is consistently below curve Ab derived from Group Ab and curve Ac derived from Group Ac. It will be observed that the values on curve Aa are also lower than those on curve A of FIG. 2, indicating that a second treatment according to the invention has additional benefits on conditioning the animals for tolerance of stress. In contrast, the values on curve Ac are higher than the values on curve A of FIG. 2, and lower than the values on curve C of FIG. 2, indicating that the effects of the treatment tend to be lost after about 24 days from the conclusion of the course of treatment, absent a second "booster" treatment according to the invention.

EXAMPLE 5

Figure 7:
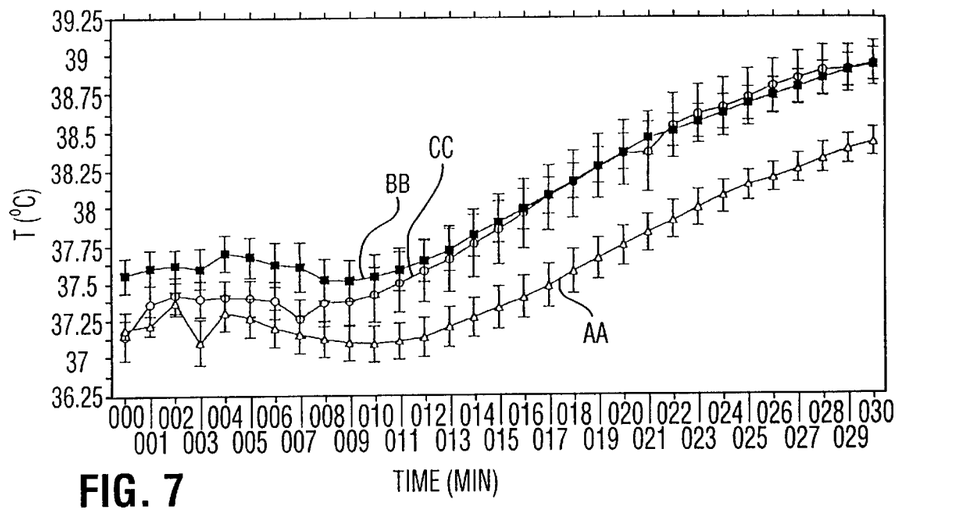
FIG. 7 is a graphical presentation of the body temperature results obtained according to Example 5 described below.

The stress responses of animals from Example 1 which had been given two courses of injection with the same fluid (saline followed by saline, untreated blood followed by untreated blood, and treated blood followed by treated blood), at 7 weeks of age and 12 weeks of age, were measured during a second immobilization stress test, conducted as previously described, on animals aged 16 weeks. The results obtained from body temperature measurements are shown on FIG. 7, a graph of body temperature against time during the 30-minute stress test, similar to FIG. 2. Curve AA is derived from the measurements (average of 5 animals) of animals which had received two courses of ten daily injections of blood treated according to the invention. Curve BS is derived from the measurements (average of 5 animals) of animals which received two such courses of injections of untreated blood. Curve CC is derived from the measurements (average of 5 animals) of animals which received two such courses of saline injections. As the Figure shows, the values obtained from animals treated according to the process of the present invention are consistently and significantly (p=0.0001) lower than those derived from the other two groups.

Figure 8:
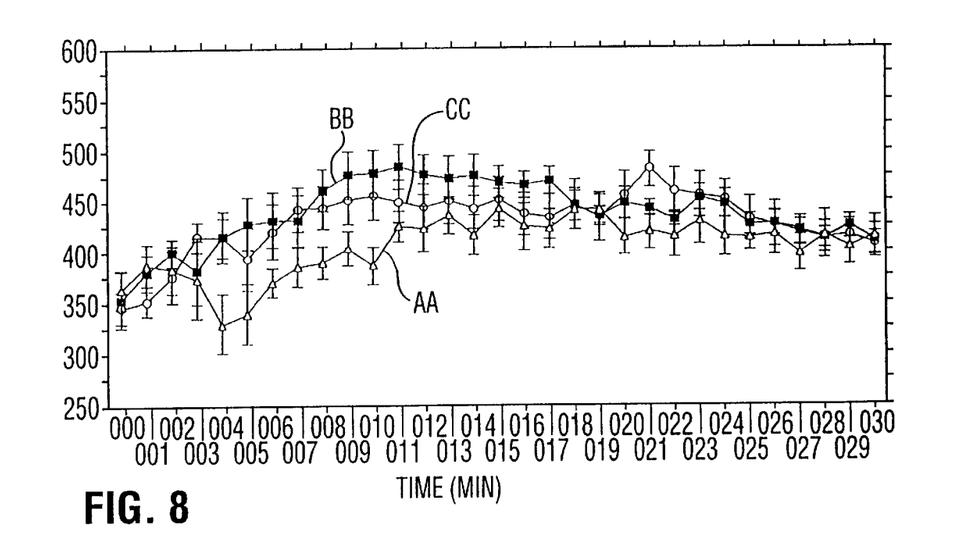
FIG. 8 is a graphical presentation of the heart rate results obtained according to Example 5 described below.

FIG. 8 of the accompanying drawings similarly presents the heart rate measurements for the three groups, during the stress test. Again, Curve AA derived from animals which had received two courses of injection of blood treated according to the invention is significantly (p=0.0001) lower than the other two curves.

EXAMPLE 6

In further demonstrations of the use of the process of the present invention in preconditioning mammalian body organs and tissues against the adverse effects of ischemic stress and subsequent reperfusion, experiments were performed on genetically hypertensive rats (SHRs), of the type previously described, by inducing ischemia in the animals' kidneys after they had been treated by the process of the invention. The procedure was as follows:

A group of 63 SHRs was divided into two approximately equal sub-groups, A and B. Sub-group A was given two courses of injections of blood from the pool described in Example 1, the injected blood having been treated with ultraviolet light, ozone-oxygen gas and elevated temperature stressors simultaneously, also as described in Example 1. The first course of injections started at age 7 weeks, and comprised 10 injections, over a period of 10 days, of a 150 µl aliquot of the treated blood intragluteally injected. The second course of injections commenced at age 12 weeks, and comprised 10 injections, administered daily, of the same volumes of treated blood ad ministered in the same manner. The animals of sub-group B were given injections of physiological saline, at the same times and in the same quantities, and thus acted as controls.

One day following the second course of injections, the rate were anaesthetized under light gas anaesthesia, and the right kidney of each animal was removed through back incision. An occlusive clip was placed on the remaining renal artery and vein, to expose the left kidney to transient ischemia, for 60 minutes. The skin was temporarily closed by clips. The animals were then followed with respect to the degree of injury resulting from the ischemia and/or the subsequent reperfusion, by taking blood samples for determining serum creatinine and blood urea nitrogen (BUN) and by determining survival rates. After taking the initial blood sample, the skin was definitively closed.

Figure 9:
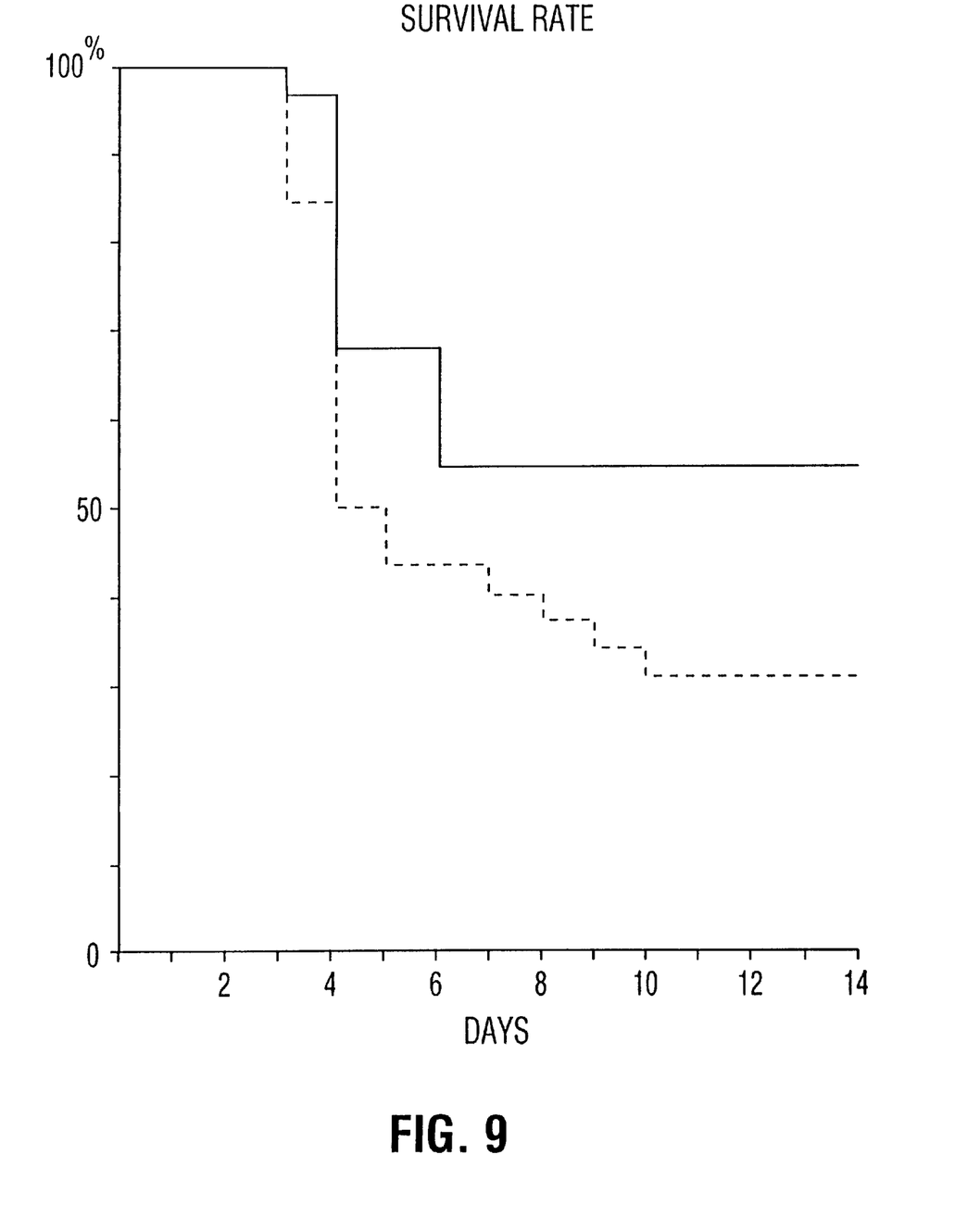
FIGS. 9, 10, 11 and 12 are graphical presentations of results obtained according to Example 6 below.

The survival rate was monitored by daily count of survivors. After 14 days, 55% of the sub-group A animals which had received the treated blood injections were surviving, compared with only 32% of the sub-group B, saline—saline treated animals. The survival rates are shown in more detail on accompanying FIG. 9, a plot of percentage of survivors as ordinate against days after renal ischemia as abscissa. On FIG. 9, the solid line derives from the results from the animals of sub-group A, and the dotted line derives from the results from the animals of sub-group B.

The results show a significant (p<0.05, log rank test), improvement in animals which received treatment according to the invention, indicating successful preconditioning against injury resulting from the ischemia and/or the subsequent reperfusion, by the process of the invention.

Blood samples of volume 100–200 µl were taken from the surviving re-perfused animals at days 1, 3, 6 and 12 after the ischemia, from the tail artery, and were analysed for creatinine content and for blood urea nitrogen (BUN) content. High creatinine content indicates impaired renal function, in that kidneys are not functioning to clear creatinine content from the blood adequately. BUN content is similarly a measure of the efficiency of renal function—the lower the BUN and creatinine content of the blood, the more efficient the renal function. Both tests are standard determinations of renal function in mammalian patients.

Figure 10:
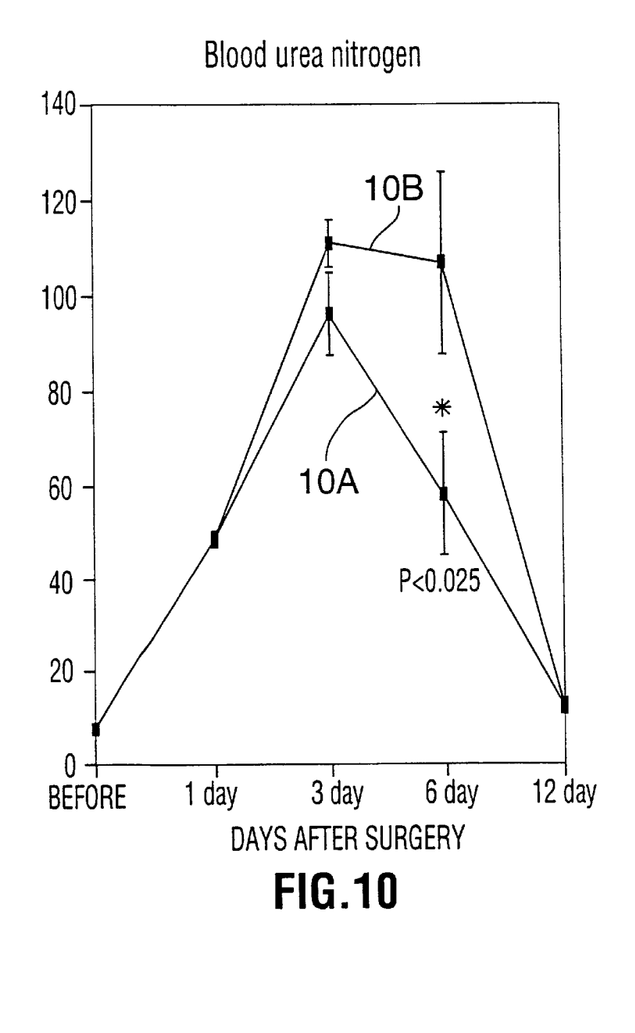

FIG. 10 of the drawings is a graphical presentation of the results of the BUN content determinations, averaged over each group of animals. Each curve is a plot of BUN values against days after ischemia. Curve 10B is derived from control sub-group B animals, curve 10A from sub-group A animals which received the treated blood. At day 6, the average BUN value for sub-group A animals was significantly lower (p=<0.025).

Figure 11:
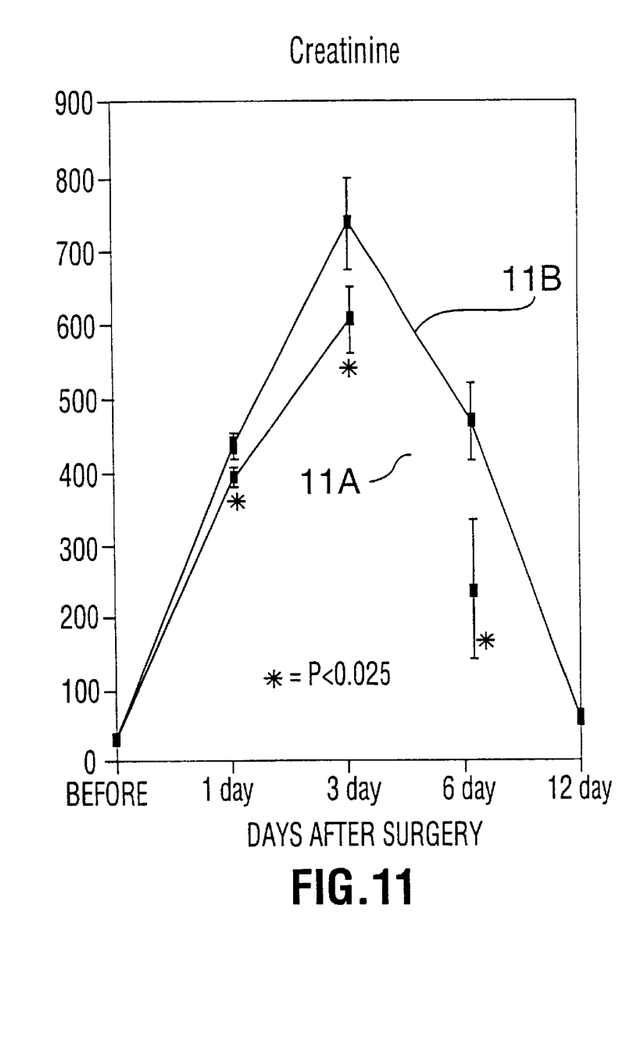

FIG. 11 of the accompanying drawings similarly gives a graphical presentation of the results of serum creatinine measurements, with the averaged curve 11A from the treated, sub-group A animals being consistently and significantly lower than the averaged curve from the control sub-group B animals, at days 1, 3 and 6 (p=<0.025). These results show consistently lower creatinine levels and lower BUN levels in samples from animals receiving treatment according to the invention, demonstrating that the treatment effectively preconditions the individual organs and tissues of the body for better resistance to subsequent ischemia stress and/or reperfusion injury.

Figure 12:
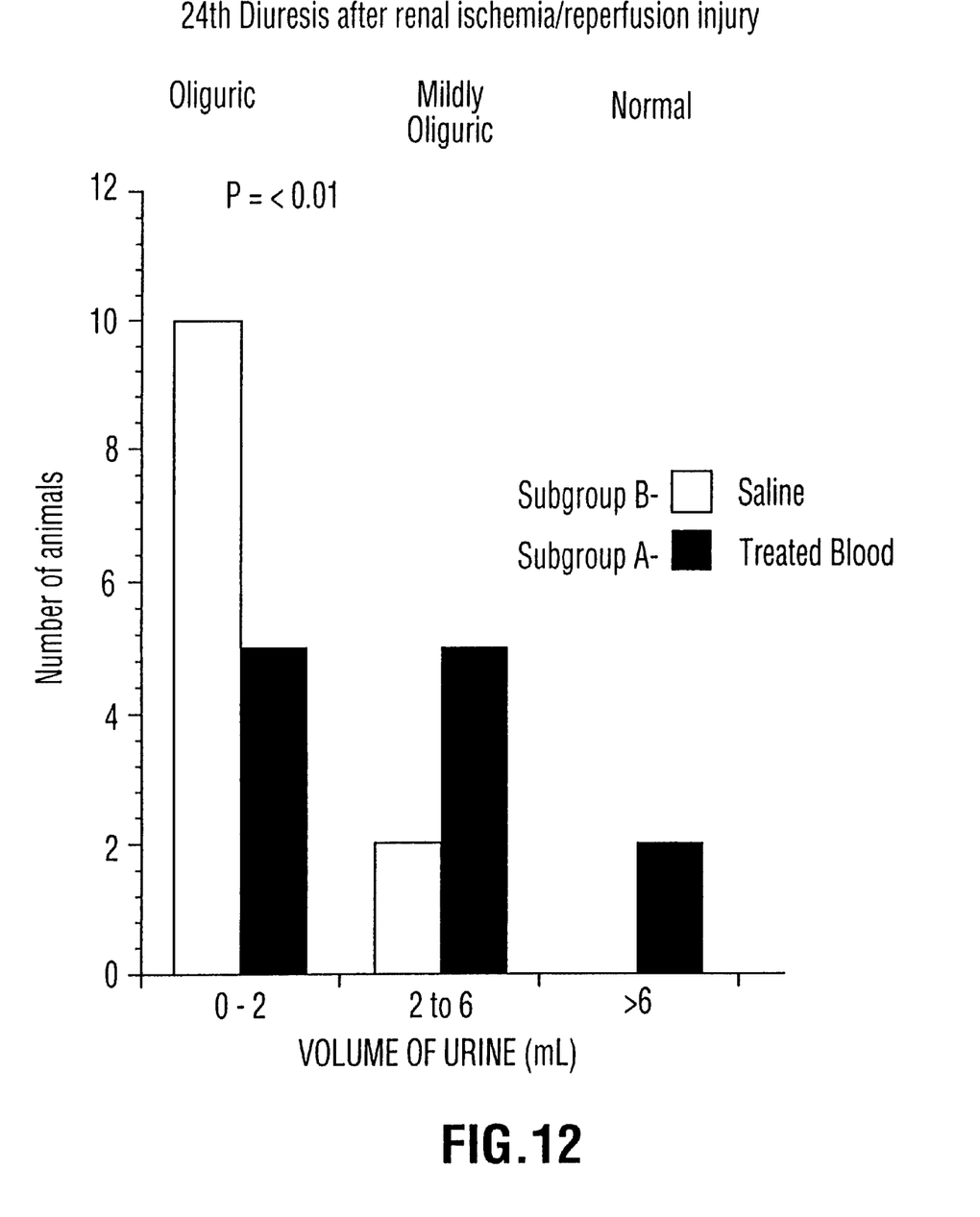

The increase in creatinine and BUN in each sub-group peaked at day 3, with a return to basal values at day 12. This peak increase in the sub-group A animals is significantly lower. Six days after ischemia/reperfusion, the levels of both creatinine and BUN in the samples from the sub-group A animal are about half those in the samples from the control animals. In the first 24 hours after ischemia, 83% of the rats in control sub-group B were oliguric (less than 2 ml of urine passed in 24 hours) whereas oliguria was present in only 42% of the sub-group A rats (p<0.01). This is shown in accompanying FIG. 12, a bar plot of number of animals in each group passing urine during the 24 hours after renal ischemia/reperfusion in volume appropriate to classify the animals as oliguric, mildly oliguric or normal. The solid bars on FIG. 12 derive from the animals of sub-group A, the open bars from the animals of sub-group B.

EXAMPLE 7

SHR male rats, 60 in total, were divided into five groups of 12 animals per group. Samples of pooled blood from sacrificed SHR rats of the same strain were given four different stressor treatments as described in Example 1 but using the following, simultaneously applied stressor combinations:

1. bubbling $O_2/O_3$ gas mixture while being subjected to UV light at elevated temperature of 42.5° C. maintained by IR lamps;
2. bubbling $O_2/O_3$ gas mixture while being subjected to UV light;
3. bubbling $O_2/O_3$ gas mixture while being maintained at elevated temperature (42.5° C.) by IR lamps; and
4. bubbling $O_2$ gas while maintained at 42.5° C. by IR lamps and being subjected to UV light (this does not constitute an oxidative environment).

The stressor quantities, times, intensities etc. were as detailed in Example 1.

The treated blood samples were administered to the respective groups 1, 2, 3 and 4 of animals, group 5 receiving physiological saline in the same quantities and at the same regimen, namely, intramuscular injection of 150 µl daily for a first course of 10 days commencing when the animals were 7 weeks old, and a second, similar course for 10 days when the animals were 12 weeks old. This is described in Example 6.

One day following the completion of the second course of injection, the animals were anaesthetized and subjected to uninephrectomy as in Example 6. The remaining left kidney was exposed to transient ischemia for 60 minutes by occluding the remaining renal artery. Survival rates were monitored for 8 days after ischemia and reperfusion. Urinary outputs were measured during the 24 hours following surgery.

Figure 13:
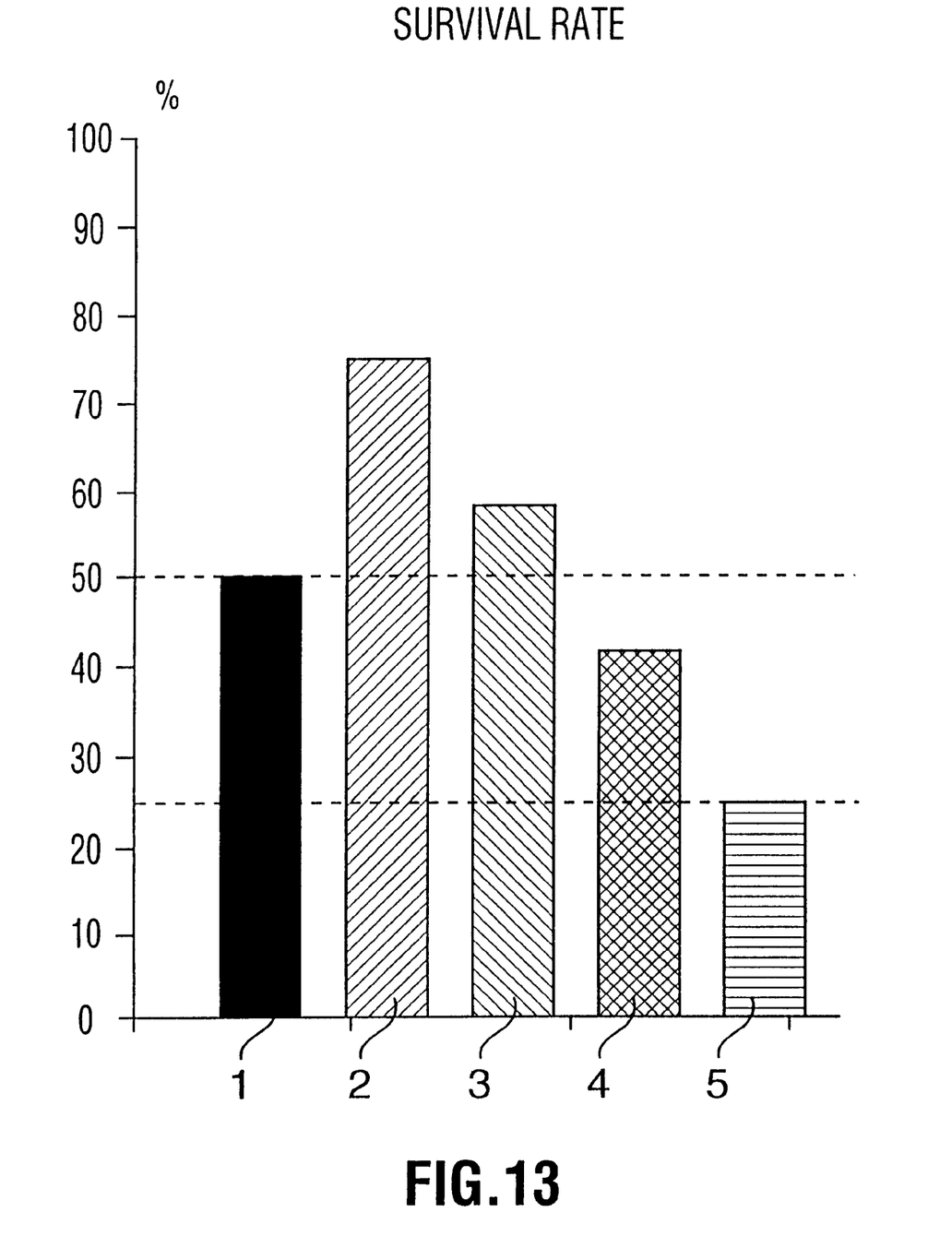
FIGS. 13 and 14 are graphical presentation of results obtained according to Example 7 below.

FIG. 13 of the accompanying drawings shows the survival rates of animals in the various groups, 8 days after surgery. Group 5, the control group which received saline injections had only a 25% survival rate, with all of the other groups significantly better. Group 2 which received blood treated with the oxidative stressor and UV light, was particularly good, with a 75% survival rate, indicating very good preconditioning to withstand subsequently encountered ischemic-reperfusion stresses.

Figure 14:
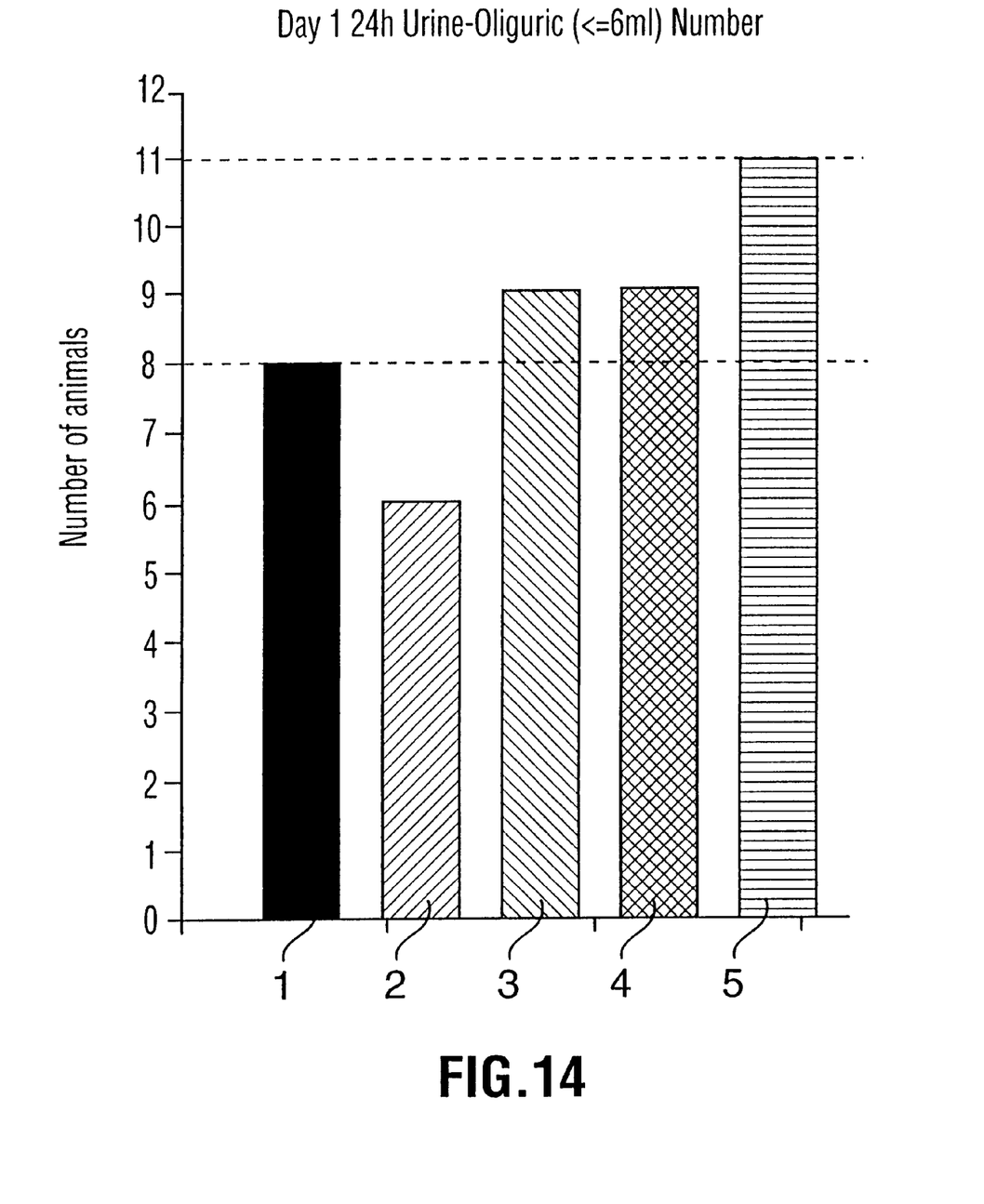

FIG. 14 of the accompanying drawings presents the results of urine output measurements, with an output of 6 ml or less of urine during the 24 hour period following surgery being determinative of oliguric animals, i.e. seriously impaired or non-existent kidney function. The number of oliguric animals is presented on the vertical axis. The highest number of oliguric animals is observed in the control group 5, with all groups treated according to the present invention significantly improved.

EXAMPLE 8

The experimental procedure of Example 6 demonstrating the use of the process in preconditioning against ischemic stress and reperfusion in an ischemic in vivo kidney test, was performed on experimental dogs, namely pure-bred normal beagles age 1–2 years, equal numbers of males and females in each group and sub-group.

Thus the animals were separated into four groups, A, B, C and D, each group consisting of 6 animals, 3 males and 3 females. Animals of groups A and C were subjected to the process of the invention, by being two 10-day courses of daily blood aliquot (3 ml) removal, extracorporeal treatment of the blood aliquot with ozone/oxygen, UV radiation and heat as described in Example 6, and re-administration of the treated aliquot to the same animal, by intramuscular injection. Each animal experienced a three-week rest period between the 10-day courses of treatment. Groups B and D were control groups, given two 10-day courses of daily injections of 3 ml of physiological saline, with a three-week rest period between the 10-day courses.

One day following the second course of injections, the animals were anaesthetized under light gas anaesthesia, and the right kidney of each animal was removed through back incision. An occlusive clip was placed on the remaining renal artery and vein, to expose the left kidney to transient ischemia, for 60 minutes. Blood samples were subsequently taken from the animals, and analysed for creatinine and blood urea nitrogen, the indicators of impaired renal function as described in Example 6.

Figure 15:
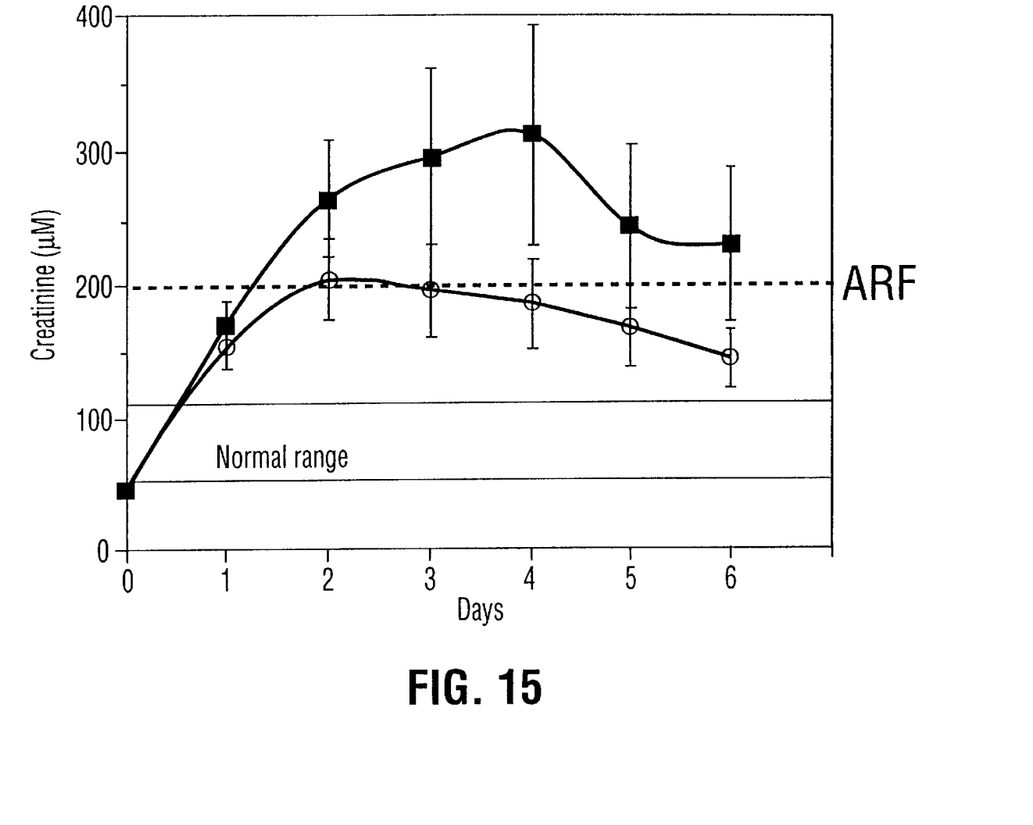
FIG. 15 is a graphical presentation of the results of Example 8.

The creatinine results are presented graphically on accompanying FIG. 15, a plot of blood creatinine content against time, over a period of 6 days following ischemia. Curve AC, of results obtained from group A and group C animals, is consistently lower than curve BD of results from control groups B and D, indicating significantly better renal functional for the dogs treated by the process of the invention. The notation ARF indicates acute renal failure. The changes over time within groups are highly significant ($p<0.0001$).

Injury to an organ subjected to ischemia can occur as a consequence of the ischemia alone (e.g. in cases where ischemia is caused by a blood clot which is subsequently dissolving, but blood does not flow back into the affected area of the organ after the clot is dissolved—the so-called "no-reflow" phenomenon), or by the subsequent reperfusion of the organ with blood after ischemia, when leukocytes or free radicals or the like may damage the blood vessels and cells of the organ. The term "injury resulting from ischemia and/or reperfusion" and the term "ischemia/reperfusion injury" as used herein cover both types of injury, occurring alone or in combination.

The above results of the procedure of the present invention can protect the kidney from injury resulting from ischemia and/or reperfusion, as measured by survival rate, blood urea and creatinine levels and urinary flow in the SHR. This indicates use of the procedure in protecting body organs in general from ischemia/reperfusion injury, including the heart, the liver, the brain, the spinal cord and other vital organs and tissues as well as the kidney, and indicates practical application of the procedure on patients scheduled to undergo surgical procedures involving ischemia/reperfusion of a body organ, such as surgical repair, removal or transplantation of a body organ.

In particular, ischemic acute renal failure is an important clinical problem with high morbidity and high mortality. The process of the present invention presents a novel approach to combatting this disorder. It can be adopted prior to kidney transplantation, on either or both the donor or recipient. It can be adopted prior to kidney revascularization. It can be adopted prior to invasive evaluation in high risk subjects, e.g. angiography in diabetics. It can be adopted prior to abdominal aortic surgery such as aortic aneurism repair and renal bench surgery (i.e. where the kidney is temporarily removed and operated on ex vivo, and then re-implanted).

As regards its use in connection with procedures involving the heart, the procedure of the invention can be conducted prior to coronary angioplasty, and bypass, or prior to transplantation, as in the case of the kidney. It is indicated for use with patients about to undergo open heart surgery with cardio-pulmonary bypass for coronary artery bypass grafting, valve replacement or surgical repair of congenital or acquired cardiac structural abnormalities. In the case of the brain or other vital organs and tissues including the intestines, the kidneys and limbs, the procedure of the invention can be used prior to angioplasty or endarterectomy, in high risk subjects.

The use of the process of the present invention prior to general anaesthesia in connection with major surgery can be viewed as general pre-conditioning of the body, to better withstand ischemia-reperfusion injuries to which the major organs will later be subjected. It is indicated for use prior to conducting major surgical procedures involving general anaesthesia in patients known to have or likely to have a significant degree of underlying atherosclerosis in the arteries supplying the brain, heart, liver, intestine, spinal cord, kidneys or limbs, the atherosclerosis rendering them more susceptible to a thrombo-ischemic event in the operative or post-operative period. Such similar general pre-conditioning of the body by the process of the invention is also indicated for use in alleviating the effects of subsequently encountered shock, leading to under-perfusion of vital organs and tissues through failure to cardiac action loss of blood or other body fluids, excessive dilation of blood vessels and excessively low blood pressure. Examples include major blood loss, trauma, sepsis and cardiogenic shock. Individuals likely to be exposed to such hazards, including patients awaiting surgery, rescue and relief crews for natural disasters, would be beneficiaries of the process of the invention.

Other areas of utility of the procedure of the present invention, in connection with preconditioning of a patient body and body organ prior to subjection to stress, e.g. ischemic stress as part of a surgical procedure, general psychological stress or physiological stress, as part of surgery or other foreseeable stress-situations, will be apparent to those skilled in the art.

References

1. Gersh, B. J., Braunwald, E., and Rutherford, J. D.: Mechanism of Cardiac Contraction and Relaxation. In:

"Heart Disease: Textbook of Cardiovascular Medicine" Braunwald, E. Ed. W. B. Saunders Company, Philadelphia, 5th Edition, pages 360–393, 1997.

What is claimed is:

1. Process for preconditioning a mammalian patient to better withstand the adverse effects of ischemic stress encountered following subsequent surgery which results in ischemia-reperfusion of cells, tissues and/or a body organ of the patient, which comprises:

extracting an aliquot of the patient's blood;

subjecting said aliquot of blood extracorporeally to at least one stressor selected from an oxidative environment, UV radiation and elevated temperature up to about 45° C., and injecting the so-treated aliquot of blood into the patient.

2. The process according to claim 1 wherein the blood aliquot is of volume about 0.1 ml to 400 ml.

3. The process according to claim 2 wherein the chosen stressor or combination of stressors is applied to the blood aliquot for a period of time from 0.5–60 minutes.

4. The process according to claim 3 wherein the oxidative environment stressor to which the blood aliquot is subjected is a mixture of medical grade oxygen and ozone, with an ozone content from about 0.1–100 µg/ml.

5. The process according to claim 3 wherein the ultraviolet radiation stressor is ultraviolet radiation from UV lamps emitting primarily at wavelengths of 280 nm or shorter.

6. The process according to claim 3 wherein the elevated temperature stressor is a temperature in the range from about 38–43° C.

7. The process according to claim 3 wherein the aliquot of blood is subjected to the oxidative environment stressor and the UV radiation stressor simultaneously.

8. The process according to claim 3 wherein the aliquot of blood is subjected to the oxidative stressor and the elevated temperature stressor simultaneously.

9. The process according to claim 3 wherein the aliquot of blood is subjected to the UV radiation stressor and the elevated temperature stressor simultaneously.

10. The process according to claim 3 wherein the blood aliquot is subjected to all three said stressors simultaneously.

11. The process according to claim 10 wherein the elevated temperature stressor is applied by infra-red radiation.

12. Process for protecting mammalian donor organs destined for transplantation from a mammalian donor to a mammalian recipient, which comprises extracting an aliquot of blood from the donor, subjecting the aliquot of extracorporeally to at least one stressor selected from an oxidative environment, UV radiation and elevated temperature up to about 45° C., and injecting the so-treated aliquot of blood into the donor prior to the removal of the organ therefrom.

13. The process according to claim 1 wherein the ischemic stress is ischemia-reperfusion of the patient's kidney, heart, liver, intestine, spinal cord or brain.

14. The process according to claim 1 wherein the ischemic stress is ischemia-reperfusion of the kidney.

15. The process according to claim 1 in which the patient suffers from atherosclerosis and is scheduled for general anaesthesia prior to ischemia of a vital organ in a surgical procedure.

16. The process according to claim 1 in which the patient is scheduled to undergo open-heart surgery or heart transplantation with cardio-pulmonary bypass.

17. The process according to claim 1 which comprises subjecting an aliquot of the mammalian patient's blood extracorporeally to infrared radiation, and reinjecting the so-treated blood aliquot into the patient.

18. The process according to claim 1 wherein the patient is scheduled to undergo aortic aneurysm repair.

19. The process according to claim 17 wherein the aliquot of blood is subjected extracorporeally to infra-red radiation in combination with an oxidative environment and/or UV radiation.

20. The process according to claim 1 in which the patient suffers from atherosclerosis and is scheduled for surgery.

21. The process according to claim 20 comprising a plurality of injections of blood aliquots which have been subjected to said stressors, administered at intervals of at least once per day.

22. The process according to claim 10 wherein the oxidative environment stressor to which the blood aliquot is subjected is a mixture of medical grade oxygen and ozone, with an ozone content from about 0.1–100 µg/ml, the ultraviolet radiation stressor is ultraviolet radiation from UV lamps emitting primarily at wavelengths of 280 nm or shorter, and the elevated temperature stressor is a temperature in the range from about 38–43° C.

23. The process according to claim 12 wherein the blood aliquot is of volume about 0.1 ml to 400 ml.

24. The process according to claim 23 wherein the chosen stressor or combination of stressors is applied to the blood aliquot for a period of time from 0.5–60 minutes.

25. The process according to claim 24 wherein the oxidative environment stressor to which the blood aliquot is subjected is a mixture of medical grade oxygen and ozone, with an ozone content from about 0.1–100 µg/ml.

26. The process according to claim 24 wherein the ultraviolet radiation stressor is ultraviolet radiation from UV lamps emitting primarily at wavelengths of 280 nm or shorter.

27. The process according to claim 24 wherein the elevated temperature stressor is a temperature in the range from about 38–43° C.

28. The process according to claim 24 wherein the aliquot of blood is subjected to the oxidative environment stressor and the UV radiation stressor simultaneously.

29. The process according to claim 24 wherein the aliquot of blood is subjected to the oxidative stressor and the elevated temperature stressor simultaneously.

30. The process according to claim 24 wherein the aliquot of blood is subjected to the UV radiation stressor and the elevated temperature stressor simultaneously.

31. The process according to claim 24 wherein the blood aliquot is subjected to all three said stressors simultaneously.

32. A process of preconditioning a mammalian patient susceptible to psychological stress, to better withstand the adverse effects of subsequently encountered psychological stresses, which comprises:

selecting a patient susceptible to psychological stress;

extracting an aliquot of said selected patient's blood;

subjecting said aliquot extracorporeally to at least one stressor selected from the group consisting of an oxidative environment, UV radiation and elevated temperature up to about 45° C.; and injecting the so-treated aliquot of blood into said selected patient.

33. The process according to claim 32 wherein the blood aliquot is of volume about 0.1 ml to 400 ml.

34. The process according to claim 33 wherein the chosen stressor or combination of stressors is applied to the blood aliquot for a period of time from 0.5–60 minutes.

35. The process according to claim 34 wherein the oxidative environment stressor to which the blood aliquot is subjected is a mixture of medical grade oxygen and ozone, with an ozone content from about 0.1–100 µg/ml.

36. The process according to claim 34 wherein the ultraviolet radiation stressor is ultraviolet radiation from UV lamps emitting primarily at wavelengths of 280 nm or shorter.

37. The process according to claim 34 wherein the elevated temperature stressor is a temperature in the range from about 38–43° C.

38. The process according to claim 34 wherein the aliquot of blood is subjected to the oxidative environment stressor and the UV radiation stressor simultaneously.

39. The process according to claim 34 wherein the aliquot of blood is subjected to the oxidative stressor and the elevated temperature stressor simultaneously.

40. The process according to claim 34 wherein the aliquot of blood is subjected to the UV radiation stressor and the elevated temperature stressor simultaneously.

41. The process according to claim 34 wherein the blood aliquot is subjected to all three said stressors simultaneously.

* * * * *